(12) United States Patent
Ramazanov

(10) Patent No.: US 8,367,072 B2
(45) Date of Patent: Feb. 5, 2013

(54) COMPOSITION FOR TREATING OBESITY AND METHOD OF USING THE SAME

(75) Inventors: Zakir Ramazanov, Chester, NY (US); Svetlana Ramazonova, legal representative, Warwick, NY (US)

(73) Assignee: Polifenoles Naturales, S.L., Las Palmas (ES)

(*) Notice: Subject to any disclaimer, the term of this patent is extended or adjusted under 35 U.S.C. 154(b) by 289 days.

(21) Appl. No.: 12/000,149

(22) Filed: Dec. 10, 2007

(65) Prior Publication Data
US 2008/0206275 A1   Aug. 28, 2008

Related U.S. Application Data

(60) Provisional application No. 60/873,727, filed on Dec. 8, 2006.

(51) Int. Cl.
- A61K 36/02 (2006.01)
- A61K 36/03 (2006.01)
- A61K 31/7042 (2006.01)
- A61P 3/04 (2006.01)
- A01N 43/20 (2006.01)

(52) U.S. Cl. .................................................. 424/195.17

(58) Field of Classification Search .................. None
See application file for complete search history.

(56) References Cited

U.S. PATENT DOCUMENTS

2002/0010141 A1* 1/2002 Ingram
2006/0167098 A1* 7/2006 Fromenty

FOREIGN PATENT DOCUMENTS

JP   2002265985 A * 9/2002

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Maeda, H et al. Biochemical and Biophysical Research Communications. 323 (May 2005); 392-397. Fucoxanthin from edible seaweed, Undaria pinnatifida, shows antiobesity effect through UCPI expression in white adipose tissues.*
Van Gaal, et al. 1997. The beneficial effects of modest weight loss on cardiovascular risk factors Int JObes 21(Suppl1), S5-S9.
Rock CL (2002). Carotenoids and cervical, breast, ovarian, and colorectal cancer. Epidemiology and clinical trials. Pure Appl. Chern. (2002), 74, 8,451-1459.
Paiva Sar, Russell RM (1999) r?-Carotene and Other Carotenoids as Antioxidants. J American College of Nutrition.. 18,5,426-433.
Stahl W, Sies H (1996) Lycopene: a biologically important carotenoid for humans? Arch Biochem Biophys 336: 1-9.
Holick CN, et al. Dietary Carotenoids, Serum r?-Carotene, and Retinol and Risk of Lung Cancer in the Alpha-Tocopherol, Beta-Carotene Cohort Study Am J Epidemio/2002; 156:536-5.
Maeda H, et al. (2005). Fucoxanthin from edible seaweed, Undaria pinnatifida, shows antiobesity effect through UCP1 expression in white adipose tissues. Biochem Biophys Res Com. 332(2):392-7.
Maeda H, et al. (2006) Fucoxanthin and its metabolite, fuxoxanthinol, suppress adipocyte differentiation in 3T3-L1 cells. Int J Mol Med.. 18(1):147-152.
Schonfeld-Warden NA & Warden CH (2001 ) . . . Physiological effects of variants in human uncoupling proteins: UCP2 influences bodymass index. Biochem Soc Trans 29, 777-784.
Clapham JC, et al. (2000). Mice overexpressing human uncoupling protein-3 in skeletal muscle are hyperphagic and lean. Nature 406, 415-418.
Clapham, et al. (2001). Concordant mRNA expression of UCP-3, but not UCP-2, with mitochondrial thioesterase-1 in brown adipose tissue and skeletal muscle in db/db diabetic mice. Biochem. Biocphys Res. Comm. (2001): 287(5): 1058-62.
Azain, et al. (2000) Dietary conjugated linoleic acid reduces rat adipose tissue cell size rather than cell number J Nutr 130,1548-1554.
Ostrowska, et al. (1999) Dietary conjugated linoleic acids increase lean tissue and decrease fat deposition in growing pigs J Nutr 129,2037-2042.
Wang, et al. (2004) Conjugated linoleic acid and obesity control:efficacy and mechanisms . . . Int JObes Relat Metab Disord . 28(8):941-955.
Bhattacharya, et al. (2005) The Combination of Dietary Conjugated Linoleic Acid and Treadmill Exercise Lowers Gain in Body Fat Mass and Enhances Lean Body Mass in High fat-fed male Balb/C mice. J. Nutr. (May 2000): 135(5): 1124-30.
Blankson, et al. (2000) Conjugated Linoleic Acid Reduces Body Fat Mass in Overweight and Obese Humans J Nutr. 130, 2943-2948.
Gaullier, et al. (2004). Conjugated linoleic acid supplementation for 1 y reduces body fat mass in healthy overweight humans. Am J Clin Nutr. 79(6):1118-1125.
Gaullier, et al. (2005) Supplementation with conjugated linoleic acid for 24 months is well tolerated by and reduces body fat mass in healthy, overweight humans . . . J Nutr 135(4):778-84.
Koba, et al. (2002). Dietary conjugated linolenic acid in relation to CLA differently modifies body fat mass and serum and liver lipid levels in rats. Lipids 37:343350; 631 37(4): 343-350.
Hernandez, et al. Fatty acid composition and total lipid content of seed oil from three commercial pomegranate cultivars CIHEAM, 2000. 205-209.
Yamasaki, et al. Dietary effect of pomegranate seed oil on immune function and lipid metabolism in mice Nutrition. 2006; 22(1):54-9.
Toi, et al. Preliminary studies on the anti-angiogenic potential of pomegranate fractions in vitro and in vivo. Angiogenesis. 2003;6(2):121-8.

(Continued)

Primary Examiner — Michele C. Flood
(74) Attorney, Agent, or Firm — Kramer & Amado, P.C.

(57) ABSTRACT

A composition for a medicinal or health effect of a treatment of liver fat and body fat, a reduction of blood pressure, an increase of the energy expenditure rate, a reduction of inflammatory C-reactive proteins and a reduction of plasma aminotransferase enzymes, comprising an effective amount of fucoxanthin alone or in combination with pomegranate seed oil, a pharmaceutically acceptable salt, a prodrug thereof, or a salt of the prodrug; and a method of using the same. The fucoxanthin may be used in pure form, or as a component of a brown marine vegetable extract.

12 Claims, 3 Drawing Sheets

OTHER PUBLICATIONS

Malnick, et al. Non-alcoholic fatty liver: a common manifestation of a metabolic disorder Q J Med 2003; 96: 699-709.

Poordad Nonalcoholic fatty liver disease: a review. Expert Opin Emerg Drugs. Aug. 2005;10(3):661-70.

Propst, et al. Prognosis in nonalcoholic steatohepatitis. Gastroenterology . . . 1995; 108:1607.

Nonomura, et al. Clinicopathologic study of alcohol-like liver disease in non-alcoholics; non-alcoholic steatohepatitis and fibrosis . . . Gastroenterol Jpn. 1992; 27:521-8.

Collantes, et al. Nonalcoholic fatty liver disease and the epidemic of obesity. Cleve Clin J Med 2004; 71:657-64.

Harrison, et al. 2006. New treatments for nonalcoholic fatty liver disease. Curr Gastroenterol Rep.8 (1):21-29.

Salgado, et al. 2000 Nonalcoholic fatty liver disease and obesity Acta Cir Bras. 2006 00;21 :72-78.

Eguchi, et al. Visceral fat accumulation and insulin resistance are important factors in nonalcoholic fatly liver disease. J GastroenteroL May 2006;41 (5):462-9.

Itoh S, et al. Comparison between nonalcoholic steatohepatitis and alcoholic hepatitis . . . Am J Gastroenterol. 1987; 82:650-4.

Powell, et al. The natural history of nonalcoholic steatohepatitis: a follow-up study of forty-two patients for upto21 years. Hepatology. 1990; 11:74-80.

Capron, et al. Fasting in obesity: another cause of liver injury with alcoholic hyaline? Dig Dis Sci. 1982; 27:265-8.

Sheth et al. Nonalcoholic Steatohepatitis . . . Annals of Internal Medicine, 1997,126,2: 137-145.

Eriksson, et al. Nonalcoholic steatohepatitis in obesity: a reversible condition. Acta Med Scand. 1986; 220:83-8.

Keeffe, et al. Steatosis and cirrhosis in an obese diabetic. Resolution offatty liver by fasting. Dig Dis Sci 1987; 32:441-5.

Rosental, et al. Liver morphology and function tests in obesity and during total starvation. Am J Dig Dis. 1967; 12:198-208.

Abdelmalek, et al. Two cases from the spectrum of nonalcoholic steatohepatitis. J Clin GastroenteroL 1995; 20:127-30.

Heitmann, et al. (1990) Prediction of body water and fat in adult Danes from measurement of electrical impedance. A validation study. Int. JObes 14: 789-802.

Ranneries, et al. (1998). Fat metabolism in formerly obese women. Am J Physiol Endocrinol Metab . . . 274: E155-E161.

Astrup, et al (1995) Prognostic markers for diet-induced weight loss in obese women . . . Int JObes Relat Metab Disord 19:275-278.

Vozarova, et al. 2002. High alanine aminotransferase is associated with decreased hepatic insulin sensitivity and predicts the development of type 2 diabetes . . . Diabetes 51(6): 1889-95.

Mulhall, et al. 2002. Non-alcoholic fatty liver disease: an overview. J Gastroenterol Hepatol. 17:1136-1143.

Angulo, et al. 2002.Non-alcoholic fatty liver disease. J Gastroenterol Hepatol17 (Suppl.): S186-S190.

Clark, et al. 2003 The prevalence and etiology of elevated aminotransferase levels in the United States Am J Gastroenterol 98 :960 967.

Thomsen, et al. 1994. Quantification of liver fat using magnetic resonance spectroscopy. Magn Reson Imaging 12:487-495.

Seppala-Lindroos, et al. 2002. Fat Accumulation in the Liver is Associated with Defects in Insulin Suppression of Glucose Production and Serum Free Fatty Acids Independent of.

Ryysy, et al. Hepatic fat content and insulin action on free fatty acids and glucose metabolism rather than insulin absorption are associated with insulin requirements during obesity in normal men. (Jul. 2002): J Clin Endocrinol Metab 87(7): 3023-8.

Jousilahti, et al. 2000. Serum gammaglutamyltransferase,self-reported alcohol drinking, and the risk of stroke. Stroke 31:1851-1855.

Lee, et al. 2003. Gamma-glutamyltransferase and diabetes—a 4 year follow-up study. Diabetologia 46: 359-364.

Perry, et al. 1998 . . . Prospective study of serum gamma-glutamyltransferase and risk of NIDDM. Diabetes Care 21 :732-737.

Nakanishi, et al. 2003. Serum gamma-glutamyltransferase and development of impaired fasting glucose or type 2 diabetes in middle-aged Japanese men. J Intern Med 254: 287-295.

Ford, et al. 1999 . . Body mass index, diabetes, and C-reactive protein among U.. S. adults . . . Diabetes Care 22:1971-1977.

Hak, et al. 1999. Associations of C-reactive protein with measures of obesity, insulin resistance, and subclinical atherosclerosis in healthy, middle-aged women.. Atheroscler Thromb Vasc Biol. 19(8): 1986-91.

Festa, et al. 2000. Chronic subclinical inflammation as part of the insulin resistance syndrome: the Insulin Resistance Atherosclerosis Study (IRAS). Cireu/ation102 :42-47.

Yudkin, et al. 1999. C-reactive protein in healthy subjects: associations with obesity, insulin resistance, and endothelial dysfunction: a potential role for cytokines originating from adipose tissue? Arterioscler Thromb Vasc Biol 19(4)_927-8.

Pradhan, et al. 2001. C-reactive protein, interleukin 6, and risk of developing type 2 diabetes mellitus JAMA 18:327334.

Barzilay, et al. (2001) The relation of markers of inflammation to the development of glucose disorders in the elderly: the Cardiovascular Health Study. Diabetes 50:2384-2389.

Freeman, et al. (2002) . . . C-reactive protein is an independent predictor of risk for the development of diabetes in the West Scotland Coronary Prevention Study. Diabetes.

Macy, et al. 1997. Variability in the measurement of Creactive protein in healthy subjects: implications for reference intervals and epidemiological applications Clin Chem 43(1): 52-8.

Stamler, et al. 1978. Weight and blood pressure: findings in hypertension screening of 1 million Americans JAMA 240, 16071610.

Dyer, et al. 1989. The INTERSALT study: relations of body mass index to blood pressure J Hum Hypertens 3,299-308.

Maeda H et al., Fucoxanthin from edible seaweed, *Undaria pinnatifida*, shows antiobesity effect through UCP1 expression in white adipose tissues. Biochemical Biophysical Research Communications. 332 (2005) 392-397.

Maeda H, et al. (2006) Fucoxanthin and its metabolite, fucoxanthinol, suppress adipocyte differentiation in 3T3-L1 cells. International Journal of Molecular Medicine. 18:147-152, 2006, Available online May 6, 2005.

Yamasaki, et al. Dietary effect of pomegranate seed oil on immune function and lipid metabolism in mice. Nutrition. 22 (2006) 54-59, Available online Oct. 12, 2005.

Arao et al., Dietary effect of pomegranate seed oil rich in 9cis, 1Ilrans, 13cis conjugated linolenic acid on lipid metabolism in obese, hyperlipidemic OLETF Rats. Lipids in Health and Disease. 2004, 3:24 1-7.

Ryysy et al., Hepatic fat content and insulin action on free fatty acids and glucose metabolism rather than insulin absorption are associated with insulin requirements during insulin therapy in type 2 diabetic patients. Diabetes, vol. 49, May 2000, 749-758.

* cited by examiner

COMPOSITION FOR TREATING OBESITY AND METHOD OF USING THE SAME

FIELD OF INVENTION

This invention relates to a composition for treating obesity, body and liver fat, hypertension, and reduction of inflammatory C-reactive proteins and plasma aminotransferase enzymes.

BACKGROUND OF THE INVENTION

Large epidemiological and clinical studies have provided convincing evidences for healthy promoting effects of natural carotenoids (1-3). Positive effects of natural carotenoids on human health primarily attributed to their provitamin and antioxidant activities (1-4). Natural carotenoids β-carotene, lycopene, lutein, astaxanthin and fucoxanthin are well known for their anti-cancer and superior free radicals scavenging properties (1-5). Recent studies have revealed that some carotenoids possess much more specific and unique pharmacological effects. For example, it has been reported that fucoxanthin, a carotenoid specific to brown marine vegetables, shows anti-obesity and thermogenic effects (6-8). According to the report, fucoxanthin upregulates the expression of uncoupling protein UCP 1 gene in white adipose tissue (WAT), thus contributing to reduction of visceral fat (6, 8). It was demonstrated that fucoxanthin reduced WAT in wistar rats and obese KK-Ay mice (6-8). Fucoxanthin-induced UCP1 expression in WAT stimulates oxidation of fatty acids (6-8). UCP proteins may also be involved in regulation of body weight and obesity (12-14). The induced overexpression of UCP proteins can become a new target for development of anti-obesity drugs (13, 14).

The anti-obesity properties of fucoxanthin and its metabolite fucoxanthinol are associated with their ability to inhibit the activity of glycerol-3-phosphate dehydrogenase enzyme (7). In addition, fucoxanthin and fucoxanthinol down regulates peroxisome proliferator-activated receptor γ (PPARTγ), which regulates adipogenic gene expression (7) and contributes to anti-obesity effects.

Fatty acids with conjugated double bonds acid have attracted considerable attention because of its potentially anti-obesity effects (15-17). Conjugated linoleic acids (CLAs) have been shown to reduce body fat in rodents and humans (18-20). Conjugated linoleic acid may reduce body fat mass and increase lean body mass in healthy overweight adults (18-21). Conjugated linolenic acids (CLNAs), another conjugated fatty acids, may reduce adipose tissues in rats (22). CLNAs have been suggested to modulate body fat and triacylglycerol metabolism in a manner different from that of CLAs (22), although the exact mechanism of the anti-obese action of CLAs and CLNAs remains unknown.

Punicic acid (9cis, 11trans, 13cis-conjugated linolenic acid; 9c, 11t, 13c-CLNA), a conjugated linolenic acid, is a primary fatty acid found in pomegranate seed oil (23-26). Dietary pomegranate seed oil rich in punicic acid alleviates accumulation of liver triacylglycerol (TGs) in obese, hyperlipidemic OLETF rats (26). The diet supplemented with 5% pomegranate seed oil resulted in a significant reduction of WAT weight (by 27%) compared with the feeding of control diet in OLETF rats, whereas feeding of 1% pomegranate seed oil diet didn't produce significant anti-obese effect (26). Thus, these results indicate that the anti-obesity effect of punicic acid is strongly dose-depending phenomenon. Reportedly, anti-obesity effect of punicic acid is related to its ability to suppress delta-9 desaturation in vivo, and the alleviation of hepatic TGs accumulation by dietary punicic acid is attributable to the suppression of delta-9 desaturation in OLETF rats (26).

Therefore, punicic acid possesses anti-obesity properties that can prevent the visceral fat accumulation and reduce liver fat in obese subjects. The accumulation of TGs in the liver is a primary metabolic factor that contributes to development of nonalcoholic fatty liver disease (NAFLD) that plays a major role in the development of insulin-resistance and obesity.

The term NAFLD used herein refers to a spectrum of hepatic pathology that resembles alcoholic liver disease, but appears in individuals who have low or negligible alcohol consumption (29, 30). The prevalence of NAFLD among examined overall population is approximately 9% in Western countries (31) and 1.2% in Japan (32). In Western countries the prevalence of NAFLD among obese subjects ranges from 23-31 percent (33, 34). The majority of patients with NAFLD is also overweight and obese, and has underlying insulin resistance (35). NAFLD is one of the main causes of chronic liver disease and it is believed to be the hepatic component of the metabolic syndrome. Its central features include obesity, hyperinsulinemia, peripheral insulin resistance, diabetes, dyslipidemia, and hypertension (36, 37). The severity of fatty liver was positively correlated with visceral fat accumulation and insulin resistance in both obese and non obese subjects, suggesting that hepatic fat infiltration in NAFLD may be influenced by visceral fat accumulation regardless of body mass index (37).

Surprisingly enough the pathogenesis of NAFLD is commonly encountered in acute starvation (fast weight loss), carbohydrate overload, protein-energy malnutrition, and corticosteroid therapy; thus, these are common mechanism for the accumulation of TGs in the liver. The gender also plays an important role in the development of NAFLD because it is more prevalent among women than men, although there is not sufficient evidence as to whether female hormones that may cause NAFLD are more prevalent in women (38, 39). NAFLD is seen most frequently in females who are morbidly obese and have had jejunal bypass surgery. Such females have an elevated level of plasma aspartate aminotransferase (AST) and alanine aminotransferase (ALT) (40, 41). Although weight loss was often correlated with reduction of NAFLD conditions, the effect of weight loss on fatty liver disease is not consistent (42-45).

Although edible brown marine vegetables containing 0.01-0.02% fucoxanthin and pomegranate have a long and safe history of human consumption, the effect of concentrated fucoxanthin and pomegranate seed oil on a treatment of liver fat and body fat, a stimulation of muscle protein synthesis, a reduction of blood pressure, an increase of the energy expenditure rate, a reduction of inflammatory C-reactive proteins and a reduction of plasma transaminase enzymes has not yet been studied. Furthermore, although both fucoxanthin and punicic acid have shown described pharmacological effects, any synergistic effect on a treatment of liver fat and body fat, a stimulation of muscle protein synthesis, a reduction of blood pressure, an increase of the energy expenditure rate, a reduction of inflammatory C-reactive proteins and a reduction of plasma transaminase enzymes when supplemented together has not been discovered.

Therefore, it would be useful to provide compositions for a medicinal or health effect of a treatment of liver fat and body fat, a stimulation of muscle protein synthesis, a reduction of blood pressure, an increase of the energy expenditure rate, a reduction of inflammatory C-reactive proteins and a reduction of plasma transaminase enzymes, comprising an effective amount of fucoxanthin alone or in combination with pomegranate seed oil, a pharmaceutically acceptable salt, a prodrug thereof, or a salt of the prodrug.

SUMMARY OF THE INVENTION

Various exemplary embodiments of the present invention provide a composition for treating liver fat and body fat, comprising an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil. The pomegranate seed oil may comprise punicic acid, a pharmaceutically acceptable salt of punicic acid, a prodrug of punicic acid, or a mixture thereof.

Further embodiments of the present invention provide an anti-obesity composition, comprising an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil. The pomegranate seed oil may comprise punicic acid, a pharmaceutically acceptable salt of punicic acid, a prodrug of punicic acid, or a mixture thereof.

Additional embodiments of the present invention provide a composition for reducing hypertension, comprising an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil. The pomegranate seed oil may comprise punicic acid, a pharmaceutically acceptable salt of punicic acid, a prodrug of punicic acid, or a mixture thereof.

Additional embodiments of the present invention provide a composition for increasing energy expenditure rate, comprising an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil. The pomegranate seed oil may comprise punicic acid, a pharmaceutically acceptable salt of punicic acid, a prodrug of punicic acid, or a mixture thereof.

Additional embodiments of the present invention provide a composition for reducing inflammatory C-reactive proteins and plasma transaminase enzymes, comprising an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil. The pomegranate seed oil may comprise punicic acid, a pharmaceutically acceptable salt of punicic acid, a prodrug of punicic acid, or a mixture thereof.

Additional embodiments of the present invention provide a composition for stimulating muscle protein synthesis, comprising an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil. The pomegranate seed oil may comprise punicic acid, a pharmaceutically acceptable salt of punicic acid, a prodrug of punicic acid, or a mixture thereof.

In various exemplary embodiments, the compositions according to the present invention may further comprise a vegetable oil. The vegetable oil may comprise omega-3 fatty acids. Such compositions according to the present invention may further comprise pomegranate seed oil in addition to vegetable oil. Pomegranate seed oil comprises punicic acid. The pomegranate seed oil may be used as a source of at least a portion of the punicic acid in the composition.

In various exemplary embodiments, the compositions according to the present invention may further comprise pomegranate seed oil. Pomegranate seed oil comprises punicic acid. The pomegranate seed oil may be used as a source of at least a portion of the punicic acid in the composition. The pomegranate seed oil may be the source of some or all of the punicic acid in the composition.

In various exemplary embodiments, an extract of brown marine vegetables containing fucoxanthin may be present in an amount from about 1 to 99 weight percent of the composition and pomegranate seed oil may be present as a source of punicic acid in an amount of from about 1 to 99 weight percent of the composition. The extract of brown marine vegetables may contain from 0.25% to 25% by weight fucoxanthin. In various embodiments, the extract of brown marine vegetables may contain from 1% to 15% by weight fucoxanthin. In further embodiments, the extract of brown marine vegetables may contain from 2.5% to 7.5% by weight fucoxanthin.

In various exemplary embodiments, an extract of brown marine vegetables containing fucoxanthin may be present in an amount from about 1 to 99 weight percent of the composition; and punicic acid may be present in an amount of from about 0.25 to 99 weight percent of the composition. The extract of brown marine vegetables may contain from 0.25% to 25% by weight fucoxanthin.

In various exemplary embodiments, an extract of brown marine vegetables containing from 1% by weight to 15% by weight fucoxanthin may be present in an amount from about 25 to 75 weight percent of the composition and pomegranate seed oil may be present in an amount from about 25 to 75 weight percent of the composition. The extract of brown marine vegetable oil is present in an amount sufficient to provide from 1 mg to 50 mg fucoxanthin per day, when taken orally. The pomegranate seed oil is present in an amount sufficient to provide from 1 to 1000 mg punicic acid per day.

In various exemplary embodiments, an extract of brown marine vegetable oil containing fucoxanthin may be present in an amount from about 40 to 60 weight percent of the composition and pomegranate seed oil may be present in an amount from about 40 to 60 weight percent of the composition. The extract of brown marine vegetable oil is present in an amount sufficient to provide from 1 mg to 50 mg fucoxanthin per day, when taken orally. The pomegranate seed oil is present in an amount sufficient to provide from 100 to 750 mg punicic acid per day.

In further embodiments, the composition is formulated into a dosage form such that the dosage form provides 1 to 1000 mg/day of an extract of brown marine vegetable oil containing fucoxanthin and 1 to 1000 mg/day of pomegranate seed oil. In additional embodiments, the dosage form provides 10 to 700 mg/day of an extract of brown marine vegetable oil containing fucoxanthin and 10 to 700 mg/day of pomegranate seed oil. In further embodiments, the dosage form provides 100 to 500 mg/day of an extract of brown marine vegetable oil containing fucoxanthin and 100 to 500 mg/day of pomegranate seed oil. Additional embodiments of the present invention provide an anti-obesity composition, comprising an effective amount of fucoxanthin, a pharmaceutically acceptable salt of fucoxanthin, a prodrug of fucoxanthin, or a mixture thereof; and an effective amount of punicic acid, a pharmaceutically acceptable salt of punicic acid, a prodrug of punicic acid, or a mixture thereof. The fucoxanthin may be administered in pure form, or as a component of an extract of brown marine vegetable oil. The punicic acid may be administered in pure form, or as a component of pomegranate seed oil. The composition may be used in the treatment of liver fat and body fat; in reduction of blood pressure; for increasing a patient's energy expenditure rate; for reducing inflammatory C-reactive proteins and plasma aminotransferase enzymes; or for stimulating muscle protein synthesis. The composition may comprise from 1 to 50 mg/day of fucoxanthin; and from 1 to 1000 mg/day punicic acid. In various exemplary embodiments, the composition may comprise from 5 to 30 mg/day of fucoxanthin; and from 10 to 700 mg/day punicic acid. In further embodiments, the composition may comprise from 10 to 25 mg/day of fucoxanthin; and from 100 to 750 mg/day punicic acid.

Various exemplary embodiments of the present invention provide a method of treating liver fat and body fat, comprising the step of administering to a mammal an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil.

Various exemplary embodiments of the invention provide a method of reducing blood pressure, comprising the step of administering to a mammal an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil.

Various exemplary embodiments of the present invention provide a method of increasing energy expenditure rate, comprising the step of administering to a mammal an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil.

In various exemplary embodiments of the present invention, a method of reducing inflammatory C-reactive proteins and plasma transaminase enzymes is provided. This method comprises the step of administering to a mammal an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil.

In further embodiments, the present invention provides a method of stimulating muscle protein synthesis, comprising the step of administering to a mammal an effective amount of an extract of brown marine vegetables, said extract of brown marine vegetables comprising fucoxanthin, a pharmaceutically acceptable salt of fucoxanthin, a prodrug of fucoxanthin, or a mixture thereof; and an effective amount of pomegranate seed oil.

In certain embodiments of the methods according to the present invention, compositions may further comprise a vegetable oil. Vegetable oil may comprise omega-3 fatty acids. The compositions may comprise both vegetable oil and pomegranate seed oil. Pomegranate seed oil may be used as a source of at least a portion of the punicic acid.

In another embodiment, compositions may further comprise pomegranate seed oil. Pomegranate seed oil may be used as a source of at least a portion of the punicic acid.

In various embodiments, an extract of brown marine vegetable oil containing fucoxanthin may be present in an amount from about 1 to 99 weight percent of the composition and pomegranate seed oil may be present in an amount from about 1 to 99 weight percent of the composition. Pomegranate seed oil is used as a source of at least a portion of the punicic acid.

In further embodiments, an extract of brown marine vegetable oil containing fucoxanthin may be present in an amount from about 25 to 75 weight percent of the composition and pomegranate seed oil may be present in an amount from about 25 to 75 weight percent of the composition.

In additional exemplary embodiments, an extract of brown marine vegetable oil containing fucoxanthin may be present in an amount from about 40 to 60 weight percent of the composition and pomegranate seed oil may be present in an amount from about 40 to 60 weight percent of the composition.

Suitably, compositions may be formulated in a dosage form such that the administration provides 1 to 1000 mg/day of an extract of brown marine vegetable oil containing fucoxanthin and 1 to 1000 mg/day of pomegranate seed oil.

In various exemplary embodiments, compositions may be formulated in a dosage form such that the administration provides 1 to 1000 mg/day of an extract of brown marine vegetable oil containing fucoxanthin and 1 to 1000 mg/day of pomegranate seed oil. In additional embodiments, the dosage form provides 10 to 700 mg/day of an extract of brown marine vegetable oil containing fucoxanthin and 10 to 700 mg/day of pomegranate seed oil. In further embodiments, the dosage form provides 100 to 500 mg/day of an extract of brown marine vegetable oil containing fucoxanthin and 100 to 500- mg/day of pomegranate seed oil.

In various exemplary embodiments, compositions may be formulated in a dosage form such that the administration provides 1-50 mg/day of the compound fucoxanthin and 1 to 1000 mg/day of punicic acid. In additional embodiments, the dosage form provides 5 to 30 mg/day of fucoxanthin and 10 to 700 mg/day of punicic acid. In further embodiments, the dosage form provides 10 to 25 mg/day of fucoxanthin and 100 to 750 mg/day of punicic acid. The fucoxanthin may be administered in pure form, or as a component of an extract of brown marine vegetable oil. The punicic acid may be administered in pure form, or as a component of pomegranate seed oil.

In further embodiments of the invention disclosed herein, a method of treating at least one condition selected from the group consisting of excessive liver fat and body fat; elevated blood pressure; insufficient energy expenditure rate; excessive levels of inflammatory C-reactive proteins and plasma aminotransferase enzymes; and insufficient muscle protein synthesis is presented. The method comprises the step of administering to a mammal a composition, said composition including an effective amount of fucoxanthin, a pharmaceutically acceptable salt of fucoxanthin, a prodrug of fucoxanthin, or a mixture thereof; and an effective amount of punicic acid, a pharmaceutically acceptable salt of punicic acid, a prodrug of punicic acid, or a mixture thereof. The composition may comprise from 1 to 50 mg/day of fucoxanthin; and from 1 to 1000 mg/day punicic acid. In various exemplary embodiments, the composition may comprise from 5 to 30 mg/day of fucoxanthin; and from 10 to 700 mg/day punicic acid. In further embodiments, the composition may comprise from 10 to 25 mg/day of fucoxanthin; and from 100 to 750 mg/day punicic acid.

Other aspects and embodiments of the invention are discussed below.

BRIEF DESCRIPTION OF THE DRAWINGS

For a fuller understanding of the nature and desired objects of the present invention, reference is made to the following detailed description taken in conjunction with the accompanying drawing figures wherein.

DETAILED DESCRIPTION OF THE INVENTION

Figure 1A:
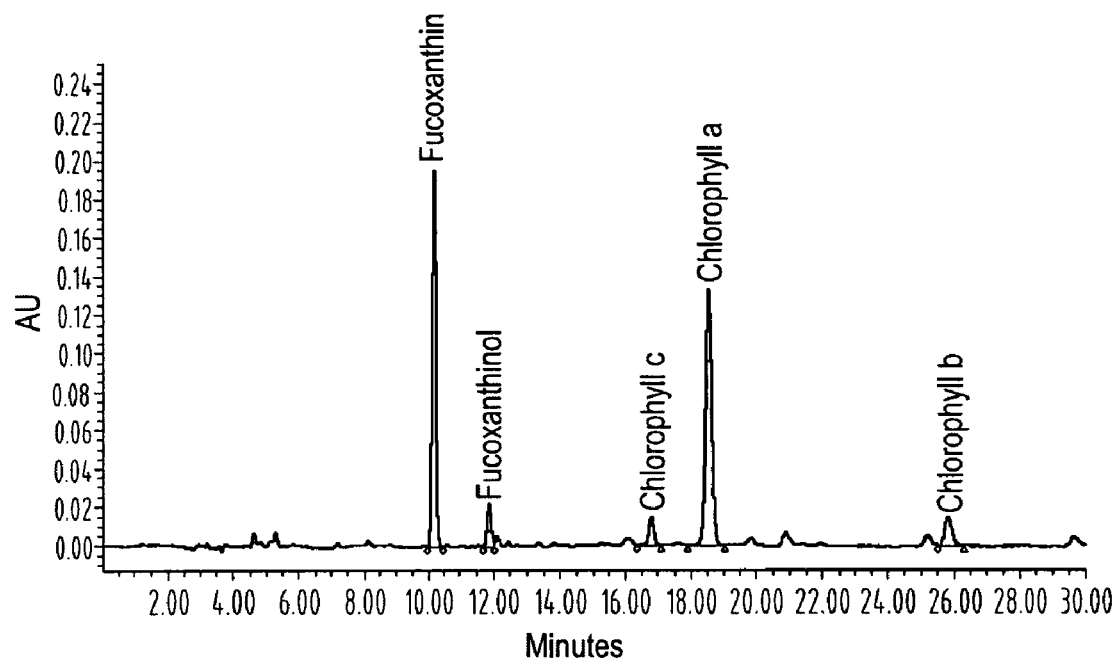
FIG. 1A is an HPLC chromatogram of brown marine vegetable extract.

Before the present composition and methods of using thereof are disclosed and described, it is to be understood that this invention is not limited to the particular configurations, as process steps, and materials may vary somewhat. It is also intended to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

As used herein, the term "dietary supplement" refers to compositions consumed to affect structural or functional changes in physiology. The term "therapeutic composition" refers to any compounds administered to treat or prevent a disease.

Fucoxanthin can be obtained from marine vegetables. More particularly, the process for obtaining fucoxanthin includes the steps of: cultivating brown marine vegetables in a photobioreactor with continuous flow of circulating deep-sea water and with illumination intensity less than full sun light intensity; washing with fresh water; freeze drying the harvested marine vegetables; and extracting pharmacologically active components. The pharmacologically active components may be extracted using supercritical $CO_2$ fluid extraction with alcohol as co-solvent. Alternatively, the pharmacologically active components may be extracted using absolute ethanol or aqueous ethanol as an extraction solvent.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed to prepare a particular therapeutic composition. The use of such media and agents for pharmaceutically active substances is well known in the art. Except insofar as any conventional media or agent is incompatible with the active ingredients, its use in the present composition is contemplated. Other ingredients known to affect the manufacture of this composition as a dietary bar or functional food can include flavorings, sugars, amino-sugars, proteins and/or modified starches, as well as fats and oils.

The dietary supplements, lotions or therapeutic compositions of the present invention can be formulated in any manner known by one of skill in the art. For example, the composition may be formulated into a capsule or tablet using conventional techniques with pharmaceutically acceptable excipients such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art.

However, the present compositions may also be formulated in other convenient forms such as, an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present composition can be formulated into cereals, snack items such as chips, bars, gumdrops, chewable candies or slowly dissolving lozenges.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. The preparations may be suitably formulated to give controlled release of the active compounds.

The present compositions and formulations thereof have a medicinal or health effect of a treatment of liver fat and body fat, a reduction of blood pressure, an increase of the energy expenditure rate, a reduction of inflammatory C-reactive proteins and a reduction of plasma transaminase enzymes.

The term "mammal" used herein refers to one selected from the group consisting of humans, non-human primates, such as dogs, cats, birds, horses, ruminants or other warm blooded animals. The invention is directed primarily to the treatment of human beings. Administration can be by any method available to the skilled artisan, for example, by oral, topical, transdermal, transmucosal, or parenteral routes.

The following examples are intended to illustrate but not in anyway limit the invention.

Example 1

The Effect of Different Dose of Experimental Sample on the Energy Expenditure on Obese Subjects Obese subjects diagnosed with NAFLD and with apparently healthy liver (HL) were matched in pairs based on age, body weight and body fat mass and were randomly divided into Experimental NAFLD group (n=36), Placebo NAFLD (n=36), Experimental HL (n=19) and Placebo-HL group (n=19). Subjects were randomly assigned, in equal numbers, to the phytomedicine experimental groups and the Placebo control group, using the Simple Randomization Procedure. Their daily dietary intake was restricted to 1800±100 kcals, of which 50±5% was in the form of carbohydrates, 30±5% from protein, and 20±5% from fat. Subjects were also instructed to consume all the foods and beverages designated by dieticians and provided by the Institute, and to eat no other food or high calories beverages. Patients were directed to take Experimental Sample and/or Placebo three times a day before meals. During the clinical phase, subjects were required to visit a designated hospital three times a week for physiological and biochemical analysis. Institute provided all foods and beverages by designated dieticians and labeled as B, L, and D for breakfast, lunch and dinner, respectively.

Food record analysis, body composition, blood and adipose biopsy samples were assessed throughout the trial. All volunteers underwent medical examination, including laboratory testing of serum alanine aminotransferase (ALT), aspartate aminotransferase (AST), γ-glutamyltransferase (GGT) enzymes activity. All participants had negative serology for hepatitis B or C. Subjects taking medications known to influence fat metabolism were also excluded.

Oral Glucose Tolerance Test

To exclude obese subjects with diabetes, standard oral glucose tolerance test with 75 g of glucose was performed as described previously. The absence of clinically manifested diabetes criteria was also included during selection procedure.

Experimental Sample

Figure 1B:
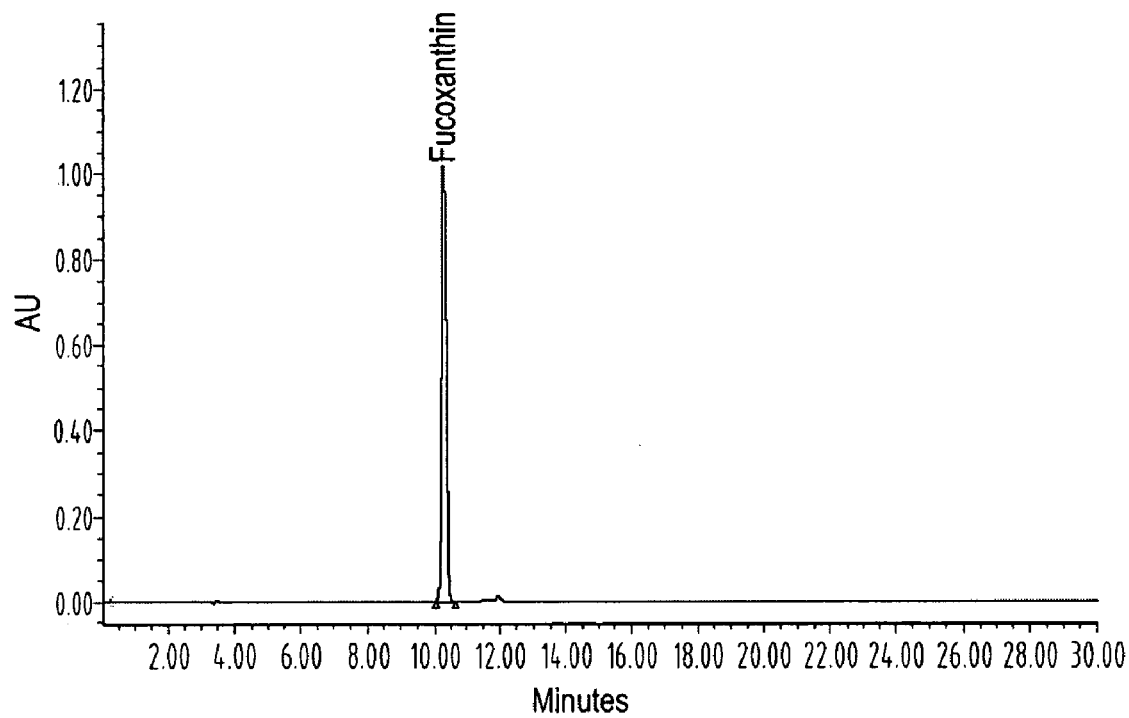
FIG. 1B is an HPLC chromatogram of Fucoxanthin reference standard.

Each capsule of experimental supplement sample used in our clinical trial was prepared from 100 mg of a brown marine vegetable extract containing 5% by weight fucoxanthin (5 mg fucoxanthin per capsule). The brown marine vegetable extract contained 30 mg marine vegetable oil (i.e., 100 mg brown marine vegetable extract contain 30% by weight marine vegetable oil, for a total of 30 mg marine vegetable oil). The brown marine vegetable extract was suspended in 100 mg cold-pressed pomegranate seed oil. The pomegranate seed oil was standardized to contain a minimum of 70% punicic acid, for a total weight of 200 mg/capsule. The content of fucoxanthin in Experimental Sample (Xanthigen) was analyzed using high performance liquid chromatography method, and the fatty acids were analyzed by Gas Chromatography method. The HPLC profile of the brown marine vegetable extract is shown in FIG. 1A, along with an HPLC chromatogram of pure fucoxanthin for comparison in FIG. 1B. The fatty acid compositions of brown marine vegetable extract and cold-pressed pomegranate seed oil are shown in Table 1.

TABLE 1

Typical fatty acid composition of brown marine vegetable extract and cold-pressed pomegranate seed oil

| Fatty acid | Brown marine vegetable (30% w/w) | Pomegranate seed oil 90% w/w) |
|---|---|---|
| 14:0 Myristic acid | 2.8 | — |
| 16:0 palmitic acid | 14.9 | 2.4 |
| 16:1 palmitoleic acid | 6.4 | 0.3 |
| 18:0 stearic acid | — | 1.2 |
| 18:1 oleic acid ω-9 | 4.5 | 5.9 |
| 18:2 linoleic acid ω-6 | 4.5 | 9.2 |
| 18:3-γ linolenic acid ω-6 | — | — |
| 18:3-α-linolenic acid ω-3 | 12.1 | 0.2 |
| 18:3 triple conjugated (Punicic acid) | — | 80.8 |
| 18:4 stearidonic acid ω-3 | 26.7 | — |
| 20:4 arachidonic acid ω-6 | 11.8 | — |
| 20:5 eicosapentaenoic acid ω-3 | 16.3 | — |

Total Weight and Body Fat Analysis

The body weight and fat mass index and visceral fat were evaluated. A total body scan was performed using dual-energy X-ray absorptiometry to determine percent body fat, lean body mass and fat mass. Fat-free mass and fat mass were calculated by the equations developed from a study using the four-compartment model on a cohort by Heitmann (1990). Height was measured to the nearest 0.5 cm and body weight to the nearest 25 g. Subjects were wearing light clothes and circumferences were taken to the nearest 0.5 cm.

Measurements of Fat Oxidation by Indirect Calorimetry

Energy expenditure (EE) and substrate oxidations were measured by indirect calorimetry as described previously (Ranneries et al., 1998). Oxygen was measured with an electrochemical oxygen sensor, and carbon dioxide was measured by an infrared carbon dioxide sensor (Ametec Carbon Dioxide Analyzer). Calculations of EE and substrate oxidation rates were performed as previously described (Astrup et al., 1991). Protein oxidation was assumed to be constant and amounting to 15% of EE. The error of calculating EE by omitting the exact correction from urinary nitrogen was negligible and impossible to estimate during such a short period of time. The reliability was assessed by the coefficient of variation on resting energy expenditure repeated every week.

After all subjects completed 16 weeks clinical trial, no adverse effect in both groups throughout the trial occurred and no evidence for increase in blood pressure or cardiac disturbances was obtained. Subjects tolerated phytomedicine Experimental supplement sample and the placebo, as well as foods designed by professional dietician and provided by the designated Hospital. The physical and anthropometrical characteristics of the subjects are given in Table 2. There was no significant difference between the two groups for any of the measurements.

TABLE 2

Physical and anthropometrical characteristics of subjects participated in the trial

| Variable | n = 41 |
|---|---|
| Age, yr | 37.4 ± 4.8 |
| Body weight, kg | 91.5 ± 4.4 |
| Body Fat, kg | 40.4 ± 3.7 |
| Liver Fat, % | 15.1 ± 2.9 |
| CRP, mg/L | 6.8 ± 3.7 |
| ALT units/L | 49 ± 11 |
| AST units/L | 50 ± 9 |
| GGT units/L | 46 ± 8 |
| Systolic Blood Pressure (mm Hg) | 130 ± 8 |
| Diastolic Blood Pressure (mm Hg) | 87 ± 7 |

Results of this clinical study, as shown in Table 3, indicated that the supplementation of Experimental Sample (Xanthigen) stimulated daily energy expenditure in obese subjects. This effect was clearly dose-dependent phenomenon. No statistically significant increase in the energy expenditure was observed in subjects who received 200 and 400 mg of Experimental Sample per day, while dramatic increase in the energy expenditure rates was observed in obese subjects who received 600 mg and 1000 mg of Experimental Sample per day, where 600 mg of Experimental Sample corresponds to 15 mg fucoxanthin and 1000 mg of Experimental Sample corresponds to 25 mg fucoxanthin. As seen in Table 3, 600 mg of Experimental Sample results in an increase in daily energy expenditure rate of 1670±310 kJ/day, which is substantially greater than that achieved with 25 mg fucoxanthin alone (1152±290 kJ/day); 600 mg of Experimental Sample also results in a change in energy expenditure rate which is vastly greater than that obtained with 600 mg placebo (58±40 kJ/day) or with 1500 mg pomegranate oil alone (159±65 kJ/day). Based on our dose-response trial, the optimum dose of Experimental Sample was established as 600 mg per day, which was used in further clinical trials.

TABLE 3

Effect of Xanthigen ™, fucoxanthin, pomegranate seed oil and olive oil on Energy Expenditure rates in obese non-diabetic female volunteers with NAFLD.

| Dosage per day, n = number of subjects | Baseline* | 2 weeks* | 5 weeks* | 10 weeks* | 16 weeks* | Change in Total Energy Expenditure (kJ/24 h) | a.P value as compared to placebo |
|---|---|---|---|---|---|---|---|
| 600 mg Placebo, n = 3 (Olive oil) | 5.91 ± 0.32 | 5.95 ± 0.26 | 5.55 ± 0.24 | 5.59 ± 0.32 | 5.95 ± 0.19 | From 8510 to 8568, Net 58 ± 40 | |
| Xanthigen ™-200 mg n = 3; 5 mg Fucoxanthin | 5.72 ± 0.22 | 5.54 ± 0.32 | 5.59 ± 0.29 | 5.67 ± 0.36 | 5.88 ± 0.31 | From 8237 to 8467, Net 230 ± 125 | P < NS** |
| Xanthigen ™-400 mg n = 3; 10 mg Fucoxanthin | 6.02 ± 0.17 | 5.98 ± 0.29 | 6.12 ± 0.31 | 6.53 ± 0.15 | 6.43 ± 0.22 | From 8668 to 9259, Net 591 ± 210 | p < 0.05 |
| Xanthigen ™ -600 mg n=4; 15 mg Fucoxanthin | 5.87 ± 0.30 | 5.68 ± 0.52 | 6.43 ± 0.43 | 6.88 ± 0.27 | 7.03 ± 0.33 | From 8453 to 10123, Net 1670 ± 310 | P < 0.05 |
| Xanthigen ™-1000 mg, n = 4; 25 mg Fucoxanthin | 5.92 ± 0.12 | 6.11 ± 0.30 | 6.47 ± 0.33 | 6.79 ± 0.21 | 7.09 ± 0.28 | From 8524 to 10210, Net 1686 ± 290 | p < 0.05 |
| Fucoxanthin, n = 4; 10 mg | 5.82 ± 0.18 | 5.69 ± 0.21 | 5.93 ± 0.15 | 5.69 ± 0.21 | 5.98 ± 0.18 | From 8381 to 8611, Net 230 ± 147 | p < NS** |
| Fucoxanthin, n = 4; 15 mg | 5.85 ± 0.27 | 5.89 ± 0.14 | 5.98 ± 0.17 | 6.11 ± 0.21 | 6.39 ± 0.17 | From 8424 to 9202, Net 778 ± 260 | p < 0.05 |
| Fucoxanthin, n = 4; 25 mg | 5.92 ± 0.16 | 6.02 ± 0.23 | 5.92 ± 0.27 | 6.29 ± 0.31 | 6.72 ± 0.22 | From 8525 to 9677, Net 1152 ± 290 | p < 0.05 |
| Fucoxanthin, n = 4; 50 mg | 6.04 ± 0.24 | 5.91 ± 0.31 | 6.32 ± 0.22 | 6.92 ± 0.31 | 7.37 ± 0.35 | From 8698 to 10613, Net 1915 ± 246 | p < 0.001 |
| Pomegranate Seed Oil, n = 4; 1500 mg | 6.01 ± 0.19 | 5.89 ± 0.32 | 5.92 ± 0.27 | 6.02 ± 0.19 | 6.12 ± 0.24 | From 8654 to 8813, Net 159 ± 65 | p < NS** |
| Pomegranate Seed Oil, n = 4; 2000 mg | 5.95 ± 0.24 | 6.00 ± 0.30 | 6.10 ± 0.26 | 6.02 ± 0.25 | 6.07 ± 0.19 | From 8568 to 8741, Net 173 ± 92 | p < NS** |

*Energy Expenditure measured in kJ/min.
**NS = Not Significant

Example 2

Effect of Experimental Sample on Plasma Serum Enzyme and Liver Fat and in Obese Subjects with NAFLD AST, ALT, and GGT are sensitive indicators of liver cell injury, and have been used to identify patients with liver disease for almost 50 years. Elevated serum ALT, ALT and GGT levels help identify many types of liver diseases in patients and have widely used to screen blood donors for non-A, non-B hepatitis. Any type of liver cell injury can modestly increase ALT, ALT and GGT levels. High plasma ALT is associated with decreased hepatic insulin sensitivity and predicts the development of type 2 diabetes (Vozarova et al., 2002). Marked elevations of these enzymes occur most often in persons with diseases that affect primarily hepatocytes, such as viral hepatitis, ischemic liver injury (shock liver), and toxin-induced liver damage. Currently, measurement of serum ALT, AST and GGT levels is the most frequently used test to identify patients with liver diseases. The levels of plasma ALT, AST and GGT are correlated strongly with BMI, obesity, and with fatty liver (NAFLD).

Patients with NAFLD are commonly characterized by elevated concentrations of markers of liver injury, including AST, ALT and GGT (Mulhall et al., 2002; Angulo, 2002). Furthermore, NAFLD has been reported to be the most common cause of chronically elevated aminotransferase levels (Clark et al., 2003). These observations indicate that AST, ALT, and other markers of liver injury may be useful surrogate measures of NAFLD and related conditions for large studies. The purpose of this study was to investigate the effects of a dietary supplement on the levels of plasma marker inflammation enzymes AST, ALT and GGT, and liver fat in the obese subjects with NAFLD.

Subjects

Seventy two (n=72) obese pre-menopausal female subjects, with an average body weight of 94.5±2.1 and average age of 34±3.5 years were recruited to take part in a double-blind, placebo-controlled, randomized clinical trial. All volunteers underwent medical examination, including laboratory testing of ALT, AST and GGT enzymes activity. All participants had negative serology for hepatitis B or C. Subjects taking medications known to influence fat metabolism were also excluded.

Liver Fat Analysis

Subjects with apparently healthy liver and NAFLD were screened and subjected to magnetic hepatic ultrasound scanning by professional physicians using Acuson 128-XP/10 scanner with a 3.5-MHz linear transducer, according to the conventional criteria. In addition, we used complementary method described previously (Thomsen et al., 1994) and Image-guided proton magnetic resonance spectroscopy method (Magnetom Vision, Siemens, Erlangen, Germany) described in details elsewhere (Seppälä-Lindroos et al., 2002). The percent liver fat was calculated by dividing 100 times $S_{fat}$ by the sum of $S_{fat}$ and $S_{water}$ (Ryysy et al., 2000).

From 140 obese subjects evaluated for NAFLD, 96 subjects were diagnosed positive for fatty liver disease. The selection criteria for NAFLD were the content of liver fat higher than 14±4%.

Experimental Supplement Sample

Each soft-gel capsules of Experimental supplement sample used in this clinical trial and placebo was prepared by Center of Modern Medicine, Institute of Immunopathology, Moscow using the method described above.

Blood and Urine Samples Collection

Venous blood and urine samples were collected into tubes containing sodium EDTA (1 g/L). Blood samples were collected once a week in the morning during 16 weeks of the trial. Plasma samples were prepared within 1 hour after the blood collection by centrifugation at 600× g for 15 min at 4°

C. Blood samples were kept in the dark and on ice until centrifugation. Plasma samples were immediately divided into aliquots and stored under argon at −70° C. Urine samples were collected at the beginning and at the end of the clinical trial. The volumes of the collected urine samples were measured and aliquots were stored at −20° C.

Serum Enzyme Analysis

Venous blood was drawn in the morning after an overnight fast. At baseline and throughout trial serum enzymes AST, ALT, and GGT activity were analyzed using the methods published in Standard Laboratory Manual. Metabolic syndrome was defined according to criteria proposed by the National Cholesterol Education Program Adult Treatment Panel III (ATP III) (Jousilahti et al., 2000; Lee et al., 2003; Perry et al., 1998; Nakanishi et al., 2003.)

Results

Patients well tolerated 600 mg Experimental Sample and no sign of adverse toxic effects was observed. Statistically significant reduction of ALT, AST and GGT was observed after 16 weeks of supplementation of Experimental Sample in all subjects. The levels of plasma ALT were reduced from its baseline 51±9 units/L to 26±7 units/L ($p<0.005$), plasma AST levels reduced from 53±7 units/L to 29±6 units/L ($p<0.005$) and GGT from 49±5 units/L to 31±5 units/L $p<0.005$). Furthermore, the level of these enzymes persisted in normal range 2 weeks after with-drove period.

Figure 2:
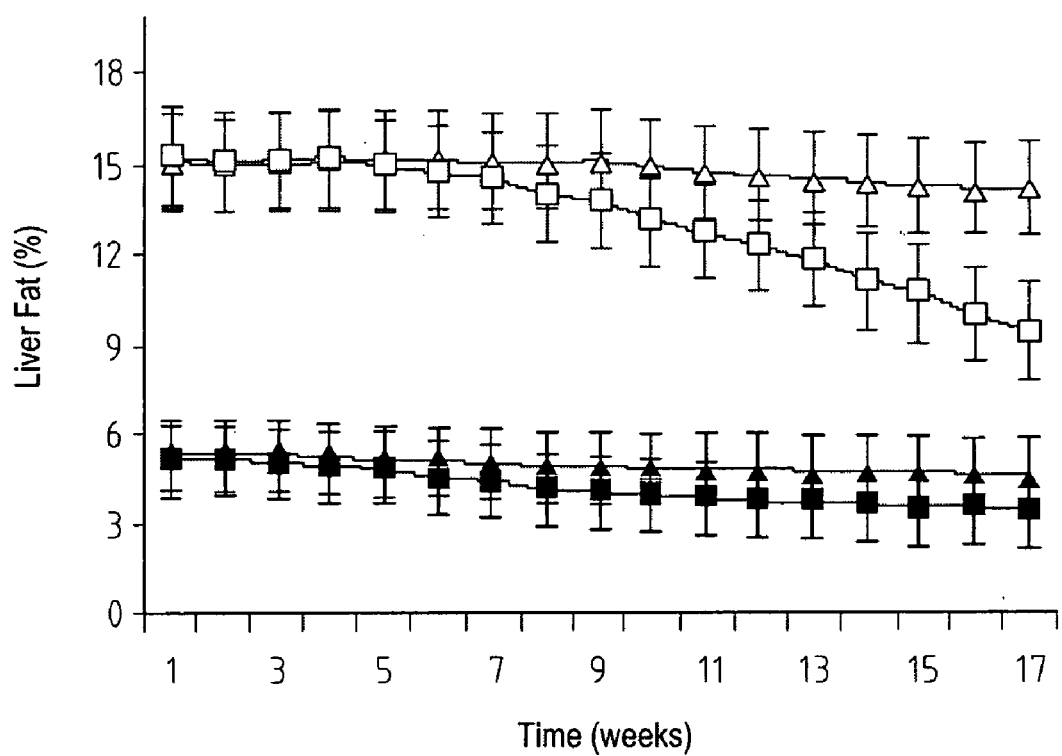
FIG. 2 shows a graph showing the effect of Xanthigen™ on liver fat content in obese subjects with nonalcoholic fatty liver disease (NAFLD) and normal liver fat content (NLF).

The reduction of plasma ALT, AST, GGT levels were correlated with significant reduction of liver fat. Statistically significant reduction of liver fat was observed after 16 weeks of Experimental Sample supplementation. The content of the liver fat was reduced from 15.3±4.1% to 9.4±3.1% ($p<0.005$) in Experimental group and 15.1±3.7% to 14.2±3.8% in the Placebo group ($p<NS$), as shown in FIG. 2. The effect of Xanthigen™ on liver fat content in obese subjects with non-alcoholic fatty liver disease (NAFLD) is seen in FIG. 2, where open triangles represent results obtained with patients on placebo and open squares represent patients receiving Xanthigen.

There was also a significant improvement in liver histology regarding features of NAFLD, steatosis, inflammation and fibrosis. Thus, these results strongly indicate that the Experimental Sample promotes significant liver fat reduction and normalize the level of plasma ALT, AST, GGT enzymes.

Plasma C-Reactive Protein Assay

C-reactive protein (CRP) is a marker of acute inflammation and is generally used as a measure of inflammatory disease. Furthermore, the levels of plasma CRP increase in obesity and type 2 diabetes (Ford et al., 1999; Hak et al., 1999). In addition, results of recent studies also indicated that an inflammatory processes increased insulin resistance (Fiesta et al. 2000) and stimulated formation of visceral fat (Yudkin et al., 1999; Pradhan et al., 2001; Barzilay et al., 2001; Freeman et al., 2002). Thus, elevated levels of CRP predict the development of insulin-resistance, metabolic syndrome, type 2 diabetes, which supports a possible role for inflammation in diabetogenesis.

C-reactive protein was measured in aliquots of blood plasma collected and stored at 70° C. A high-sensitivity, two-site enzyme-linked immunoassay was developed with use of a peroxidase-conjugated rabbit antihuman C-reactive protein antibody (DK2600, Dako, Glostrup, Denmark) and a polyclonal anti-C-reactive protein capture antibody. The lower limit of the working range of the assay was 0.1 mg per liter as described by Macy[2] et al. (1997). CRP standard serum was used for calibration.

Results

The effect of the Experimental Sample on plasma concentrations of pro-inflammatory C-reactive proteins (CRP) in the obese subjects with NAFLD is summarized in Table 4. This result indicates that the Experimental Sample supplementation significantly reduced plasma CRP from 6.6±2.7 mg/l to 3.64±2.8*mg/L ($p<0.05$) during 16 weeks of the trial, while in the placebo group from 6.3±2.7 mg/l to 5.4412.1 mg/L ($p<NS$). This result strongly indicates that Experimental Sample possesses anti-inflammatory properties.

Effect of Experimental Sample on Blood Pressure in Obese Subjects with NAFLD

Several large epidemiological studies have documented the association between body weight and blood pressure (Stamler et al., 1989; Dyer & Elliott, 1989; Van Gaal et al., 1997). The supplementation of Experimental Sample reduced significantly both systolic and diastolic blood pressure in obese subjects, while no change in blood pressure was observed in the Placebo group (Table 4). Systolic Blood Pressure of obese subjects with NAFLD was reduced from 138±6 mm Hg to 119±6 mm Hg ($p<0.05$) during 16 weeks of Experimental Sample supplementation and Diastolic Blood Pressure was reduced from 91±4 mm Hg to 79±3 mm Hg $p<0.05$).

On the other hand, no such positive changes in Systolic and Diastolic Blood Pressure was observed in the Placebo group. The correlation between reduction of the liver fat and normalization of blood pressure was largely anticipated because majority of obese subjects also develop hypertension.

TABLE 4

Pre-clinical and Post-clinical characteristics of obese subjects with fatty liver

| Variable | Preclinical Placebo, n = 36 | Preclinical Experimental Sample, n = 36 | Post-clinical Placebo, n = 36 | Post-clinical Experimental Sample, n = 36 |
| --- | --- | --- | --- | --- |
| Age, yr | 37.4 ± 2.8 | 36.1 ± 2.1 | | |
| Mass, kg | 93.5 ± 2.4 | 94.1 ± 2.1 | 92.1 ± 2.8 | 87.2 ± 3.7 |
| Fat mass, kg | 42.1 ± 1.7 | 42.3 ± 2.2 | 41.2 ± 2.3 | 37.9 ± 2.9* |
| Liver Fat, % | 15.1 ± 3.7 | 15.3 ± 4.1 | 14.2 ± 3.8 | 9.4 ± 3.1* |
| CRP, mg/L | 6.3 ± 2.7 | 6.18 ± 2.4 | 5.44 ± 2.1 | 3.64 ± 2.8* |
| ALT units/L | 51 ± 9 | 48 ± 7 | 40 ± 6 | 26 ± 7* |
| AST units/L | 53 ± 7 | 51 ± 5 | 46 ± 6 | 29 ± 6* |
| GGT units/L | 49 ± 5 | 47 ± 7 | 46 ± 6 | 31 ± 5* |
| Systolic Blood Pressure mm Hg | 136 ± 5 | 138 ± 6 | 124 ± 4 | 119 ± 6* |
| Diastolic Blood Pressure mm Hg | 88 ± 2 | 91 ± 4 | 85 ± 3 | 79 ± 3* |

Values are means ± SE.
*P < 0.05

Example 3

Effect of Experimental Sample on Liver Fat and Plasma Serum Enzyme in Obese Subjects with Healthy Liver Table summarizes the effect of Experimental Sample on biochemical and physiological characteristics of the obese subjects with healthy liver fat levels, who participated in 16 weeks clinical trial. The selection criteria for obese subjects with healthy liver fat levels were the content of liver fat less than 5.3±1.5%. Thirty eight (n=38) obese pre-menopausal female subjects, with an average body weight 94.5±2.1 kgs, average age of 34±5.7 years, and liver fat content 5.3±1.5% were recruited to take part in a double-blind, placebo-controlled, randomized clinical trial.

Results

The supplementation of 600 mg of Experimental Sample during 16 weeks of trial reduced liver fat content in obese subjects from 5.1±1.5% to 3.4±1.8% (p<0.05), and from 5.3±1.1% to 4.6±1.4% in the placebo group (p<NS), as shown in FIG. 2. The effect of Xanthigen™ on liver fat content in obese subjects with healthy livers (NLD) is seen in FIG. 2, where filled triangles represent results obtained with patients on placebo and filled squares represent patients receiving Xanthigen. Obese subjects with healthy liver fat levels also had slightly elevated levels of plasma AST, ALT and GGT, although the absolute values of these marker enzymes were significantly lower than those observed in the obese subjects with NAFLD (Table).

The Experimental Sample reduced both systolic and diastolic blood pressure in obese subjects with healthy liver as we observed previously in subjects with NAFLD (Table 5). Systolic blood pressure of obese subjects with healthy liver was reduced from 128±6 mm Hg to 112±6 mm Hg (p<0.05) during 16 weeks of Experimental Sample supplementation and Diastolic Blood Pressure was reduced from 93±2 mm Hg to 77±3 mm Hg (p<0.05). No significant change in blood pressure was observed in the Placebo group.

TABLE 5

Pre-clinical and Post-clinical characteristics of obese subjects with healthy liver

| Variable | Preclinical Placebo n = 19 | Preclinical Experimental Sample n = 19 | Post-clinical Placebo, n = 19 | Post-clinical Experimental Sample n = 19 |
|---|---|---|---|---|
| Age, years | 34.7 ± 3.5 | 35.7 ± 3.2 | | |
| Mass, kg | 93.9 ± 1.4 | 94.5 ± 2.1 | 92.5 ± 1.5 | 88.2 ± 1.9* |
| Fat mass, kg | 42.7 ± 2.4 | 43.3 ± 2.9 | 41.1 ± 2.9 | 38.1 ± 3.2* |
| Liver Fat (%) | 5.3 ± 1.1 | 5.1 ± 1.5 | 4.6 ± 1.4 | 3.4 ± 1.8* |
| ALT units/L | 31 ± 9 | 33 ± 7 | 28 ± 6 | 26 ± 7 |
| AST units/L | 33 ± 7 | 38 ± 5 | 29 ± 6 | 29 ± 2 |
| GGT units/L | 29 ± 3 | 27 ± 3 | 26 ± 2 | 21 ± 3 |
| Systolic Blood Pressure mm Hg | 126 ± 7 | 128 ± 6 | 128 ± 4 | 112 ± 6* |
| Diastolic Blood Pressure mm Hg | 92 ± 4 | 93 ± 2 | 89 ± 4 | 77 ± 3* |

Values are means ± SE.
*P < 0.05

Incorporation by Reference

All publications referenced herein and listed below are incorporated by reference in their entirety.

1 Krinsky N I (1998). Overview of lycopene, carotenoids, and disease prevention. Proc Soc Exp Biol Med 218: 95-97.
2. Rock C L (2002). Carotenoids and cervical, breast, ovarian, and colorectal cancer. Epidemiology and clinical trials. Pure Appl. Chern. (2002), 74, 8,451-1459.
3. Paiva S A R, Russell R M (1999) r?-Carotene and Other Carotenoids as Antioxidants. J American College of Nutrition. 18, 5, 426-433.
4. Stahl W, Sies H (1996) Lycopene: a biologically important carotenoid for humans? Arch Biochem Biophys 336: 1-9.
5. Holick C N, Michaud D S, Stolzenberg-Solomon R, Mayne S T, Pietinen T, Taylor P R, Virtamo J, Albanes D Dietary Carotenoids, Serum r?-Carotene, and Retinol and Risk of Lung Cancer in the Alpha-Tocopherol, Beta-Carotene Cohort Study Am J Epidemio/2002; 156:536-547.
6. Maeda H, Hosokawa M, Sashima T, Funayama K, Miyashita K. (2005). Fucoxanthin from edible seaweed, Undaria pinnatifida, shows antiobesity effect through UCP1 expression in white adipose tissues. Biochem Biophys Res Commun 332(2):392-397.
7. Maeda H, Hosokawa M, Sashima T, Takahashi N, Kawada T, Miyashita K. (2006) Fucoxanthin and its metabolite, fucoxanthinol, suppress adipocyte differentiation in 3T3-L1 cells. Int J Mol Med. 18(1):147-152.
8. Miyashita K (2006). Seaweed carotenoid, fucoxanthin, with highly bioactive and nutritional activities. J. marine Bioscience and Biotechnology. 1. 1; 48-58.
9. Schonfeld-Warden N A & Warden C H (2001). Physiological effects of variants in human uncoupling proteins: UCP2 influences bodymass index. Biochem Soc Trans 29, 777-784.
10. Clapham J C, Arch J R, Chapman H, Haynes A, Lister C, Moore G B, Piercy V, Carter S A, Lehne I, Smith S A, Beeley L J, Godden R J, Herrity N, Skehel M, Changani K K, Hockings P D, Reid D G, Squires S M, Hatcher J, Trail B, Latcham J, Rastan S, Harper A J, Cadenas S, Buckingham J A, Brand M D & Abuin A (2000). Mice overexpressing human uncoupling protein-3 in skeletal muscle are hyperphagic and lean. Nature 406, 415-418.
11. Clapham J C, Coulthard V H & Moore G B (2001). Concordant mRNA expression of UCP-3, but not UCP-2, with mitochondrial thioesterase-1 in brown adipose tissue and skeletal muscle in db/db diabetic mice. Biochem Biophys Res Commun 287, 1058-1062.
12. Azain, M J, Hausman, D B, Sisk, M B, Flatt, W P, Jewell, D E (2000) Dietary conjugated linoleic acid reduces rat adipose tissue cell size rather than cell number J Nutr 130, 1548-1554.
13. Ostrowska, E, Muralitharan, M, Cross, R F, Bauman, D E, Dunshea, F R (1999) Dietary conjugated linoleic acids increase lean tissue and decrease fat deposition in growing pigs J Nutr 129, 2037-2042.
14. Wang Y W, Jones P J. (2004). Conjugated linoleic acid and obesity control:efficacy and mechanisms. Int JObes Relat Metab Disord. 28(8):941-955.
15. Bhattacharya A, Rahman M, Sun 0, Lawrence R, Mejia W, McCarter R, O'Shea M, Fernandes G. (2005). The Combination of Dietary Conjugated Linoleic Acid and Treadmill Exercise Lowers Gain in Body Fat Mass and Enhances Lean Body Mass in High Fat-Fed Male Balb/C Mice J. Nutr., 135(5): 1124-1130.
16. Blankson, H, Stakkestad, J. A, Fagertun, H, Thom, E, Wadstein, J, Gudmundsen, 0. (2000). Conjugated Linoleic Acid Reduces Body Fat Mass in Overweight and Obese Humans J Nutr. 130, 2943-2948.
17. Gaullier J M, Halse J, Hoye K, Kristiansen K, Fagertun H, Vik H, Gudmundsen 0. (2004). Conjugated linoleic acid supplementation for 1 y reduces body fat mass in healthy overweight humans. Am J Clin Nutr. 79(6):1118-1125.
18. Gaullier J M, Halse J, Hoye K, Kristiansen K, Fagertun H, Vik H, Gudmundsen 0. (2005). Supplementation with conjugated linoleic acid for 24 months is well tolerated by and reduces body fat mass in healthy, overweight humans. J Nutr 135(4):778-84;
19. Koba K, Akahoshi A, Yamasaki M, Tanaka K, Yamada K, Iwata T, Kamegai T, Tsutsumi K, Sugano M. (2002). Dietary conjugated linolenic acid in relation to CLA differently modifies body fat mass and serum and liver lipid levels in rats. Lipids 37:343350; 631
20. Hernandez F, Meldarejo P, Olias J M, Artes F Fatty acid composition and total lipid content of seed oil from three commercial pomegranate cultivars CIHEAM, 2000. 205-209
21. Yamasaki M, Kitagawa T, Koyanagi N, Chujo H, Maeda H, Kohno-Murase J, Imamura J, Tachibana H, Yamada K.

Dietary effect of pomegranate seed oil on immune function and lipid metabolism in mice Nutrition. 2006; 22(1):54-9
22 Toi M, Bando H, Ramachandran C, Melnick S J, Imai A, Fife R S, Carr R E, Oikawa T, Lansky E P. Preliminary studies on the anti-angiogenic potential of pomegranate fractions in vitro and in vivo. Angiogenesis. 2003; 6(2): 121-8
23. Arao K, Wang Y-M, Inoue N, Hirata J, Cha J-Y, Nagao K, Yanagita T. (2004). Dietary effect of pomegranate seed oil rich in 9cis, 1llrans, 13cis conjugated linolenic acid on lipid metabolism in obese, hyperlipidemic OLETF Rats Lipids Health Dis. 3: 24.
24. Malnick S O H, Beergabel M, H. Knobler H Non-alcoholic fatty liver: a common manifestation of a metabolic disorder Q J Med 2003; 96: 699-709
25. Poordad F F Nonalcoholic fatty liver disease: a review. Expert Opin Emerg Drugs. 2005 August; 10(3):661-70
26. Propst A, Propst T, Judmaier G, Vogel W. Prognosis in nonalcoholic steatohepatitis. Gastroenterology. 1995; 108: 1607
27 Nonomura A, Mizukami Y, Unoura M, Kobayashi K, Takeda Y, Takeda R Clinicopathologic study of alcohol-like liver disease in non-alcoholics; non-alcoholic steatohepatitis and fibrosis. Gastroenterol Jpn. 1992; 27:521-8
28. Angulo P Nonalcoholic fatty liver disease. N. Engl J Med 2002; 346: 1221-31
29. Collantes R, Ong J P, Younossi Z M. Nonalcoholic fatty liver disease and the epidemic of obesity. Cleve Clin J Med 2004; 71:657-64.
30. Harrison S A 2006. New treatments for nonalcoholic fatty liver disease. Curr Gastroenterol Rep. 8 (1):21-29.
31. Salgado J W, Santos J S, Sankarankutty A K, Castro E Silva 00 Nonalcoholic fatty liver disease and obesity Acta Cir Bras. 2006 00; 21:72-78.
32. Eguchi Y, Eguchi T, Mizuta T, Ide Y, Yasutake T, Iwakiri R, Hisatomi A, Ozaki I, Yamamoto K, Kitajima Y, Kawaguchi Y, Kuroki S, Ono N. Visceral fat accumulation and insulin resistance are important factors in nonalcoholic fatty liver disease. J GastroenteroL 2006 May; 41 (5):462-9
33. Itoh S, Yougel T, Kawagoe K. Comparison between non-alcoholic steatohepatitis and alcoholic hepatitis. Am J Gastroenterol. 1987; 82:650-4.
34. Powell E E, Cooksley W G, Hanson R, Searle J, Halliday J W, Powell L W. The natural history of nonalcoholic steatohepatitis: a follow-up study of forty-two patients for upto 21 years. Hepatology. 1990; 11:74-80.
35. Capron J P, Delamarre J, Dupas J L, Braillon A, Degott C, Quenum C Fasting in obesity: another cause of liver injury with alcoholic hyaline? Dig Dis Sci. 1982; 27:265-8.
36. Sheth S G, Gordon F D, Chopra S Nonalcoholic Steatohepatitis. Annals of Internal Medicine, 1997, 126, 2: 137-145
37. Eriksson S, Eriksson K F, Bondesson L Nonalcoholic steatohepatitis in obesity: a reversible condition. Acta Med Scand. 1986; 220:83-8;
38. Keeffe E B, Adesman P W, Stenzel P, Palmer R M. Steatosis and cirrhosis in an obese diabetic. Resolution of fatty liver by fasting. Dig Dis Sci 1987; 32:441-5.
39. Rosental P, Biava C, Spencer H, Zimmermnan H J. Liver morphology and function tests in obesity and during total starvation. Am J Dig Dis. 1967; 12:198-208.
40. Abdelmalek M, Ludwig J, Lindor K D. Two cases from the spectrum of nonalcoholic steatohepatitis. J Clin GastroenteroL 1995; 20:127-30.
41. World Health Organization Expert Committee on Diabetes Mellitus (1980) WHO Expert Committee on Diabetes Mellitus: second report World Health Organ Tech Rep Ser 646, 1-80 World Health Organization Study Group (1994) Prevention of diabetes mellitus. Report of a WHO Study Group World Health Organ Tech Rep 844, 1100)
42. Heitmann, B. L. (1990) Prediction of body water and fat in adult Danes from measurement of electrical impedance. A validation study. Int. JObes 14: 789-802.
43. Ranneries C, BUlow J, Buemann B, Christensen N J, Madsen J, Astrup A (1998). Fat metabolism in formerly obese women. Am J Physiol Endocrinol Metab. 274: E155-E161
44. Astrup A, Buemann B, Gluud C, Bennett P, Tjur T, Christensen N J. (1995). Prognostic markers for diet-induced weight loss in obese women. Int JObes Relat Metab Disord 19:275-278.
45. Vozarova B, Stefan N, Lindsay R S, Saremi A, Pratley R E, Bogardus C, Tataranni P A: 2002. High alanine aminotransferase is associated with decreased hepatic insulin sensitivity and predicts the development of type 2 diabetes. Diabetes 51:1889-1895.
46. Mulhall B P, Ong J P, Younossi Z M: 2002. Non-alcoholic fatty liver disease: an overview. J Gastroenterol Hepatol. 17:1136-1143.
47. Angulo P, Linder K D: 2002. Non-alcoholic fatty liver disease. J Gastroenterol Hepatol 17 (Suppl.): S186-S190
48. Clark J M, Brancati F L, Diehl A M, 2003 The prevalence and etiology of elevated aminotransferase levels in the United States Am J Gastroenterol 98:960 967.
49. Thomsen C, Becker U, Winkler K, Christoffersen P, Jensen M, Henriksen 0 1994. Quantification of liver fat using magnetic resonance spectroscopy. Magn Reson Imaging 12:487-495.
50. Seppala-Lindroos A, Vehkavaara S, Hakkinen A-M, Goto T, Westerbacka J, Sovliarvi A, Halavaara J, Yki-Jar H. 2002. Fat Accumulation in the Liver Is Associated with Defects in Insulin Suppression of Glucose Production and Serum Free Fatty Acids Independent of Obesity in Normal Men. J Clinical Endocrin & Metabolism, 87, 7 30233028.
51. Ryysy L, Hakkinen A M, Goto T, Vehkavaara S, Westerbacka J, Halavaara J, Yki-Jarvinen H 2000 Hepatic fat content and insulin action on free fatty acids and glucose metabolism rather than insulin absorption are associated with insulin requirements during insulin therapy in type 2 diabetic patients. Diabetes 49:749-758.
52. Jousilahti P, Rastenyte D, Tuomilehto J: 2000. Serum gammaglutamyltransferase, self-reported alcohol drinking, and the risk of stroke. Stroke 31:1851-1855.
53. Lee D H, Ha M H, Kim J H, Christiani D C, Gross M D, Steffes M, Blomhoff R, Jacobs D R Jr: 2003. Gamma-glutamyltransferase and diabetes-a 4 year follow-up study. Diabetologia 46: 359-364.
54. Perry I J, Wannamethee S G, Shaper A G: 1998. Prospective study of serum gammaglutamyltransferase and risk of NIDDM. Diabetes Care 21:732-737.
55. Nakanishi N, Nishina K, Li W, Sato M, Suzuki K, Tatara K. 2003. Serum gammaglutamyltransferase and development of impaired fasting glucose or type 2 diabetes in middle-aged Japanese men. J Intern Med 254: 287-295.
56. Ford E S: 1999. Body mass index, diabetes, and C-reactive protein among U. S. adults. Diabetes Care 22:1971-1977
57. Hak A E, Stehouwer D A, Bots M L, Polderman K H, Schalkwijk C G, Westerndorp I C D, Hofman A, Witterman C M: 1999. Associations of C-reactive protein with measures of obesity, insulin resistance, and subclinical atherosclerosis in healthy, middle-aged women. Atheroscler Thromb Vasc Bioi 19:1986-1991

58. Festa A, D'Agostino R Jr, Howard G, Mykkanen L, Tracy R P, Haffner S M. 2000. Chronic subclinical inflammation as part of the insulin resistance syndrome: the Insulin Resistance Atherosclerosis Study (IRAS). Cireu/ation 102: 42-47.
59. Yudkin J S, Stehouwer C D, Emeis J J, Coppaek S W 1999. C-reactive protein in healthy subjects: associations with obesity, insulin resistance, and endothelial dysfunction: a potential role for cytokines originating from adipose tissue? Arteriose/er Thromb Vase 8; 0/19:972-978.
60. Pradhan A D, Manson J E, Rifai N, Buring J E, Ridker P M. 2001. C-reactive protein, interleukin 6, and risk of developing type 2 diabetes mellitus JAMA 18:327334.
61. Barzilay J I, Abraham L, Heckbert S R, Cushman M, Kuller L H, Resnick H E, Tracy R P (2001) The relation of markers of inflammation to the development of glucose disorders in the elderly: the Cardiovascular Health Study. Diabetes 50:2384-2389.
62. Freeman D J, Norrie J, Caslake M J, Gaw A, Ford I, Lowe G D, O'Reilly D S, Packard C J, Sattar N. (2002). C-reactive protein is an independent predictor of risk for the development of diabetes in the West Scotland Coronary Prevention Study. Diabetes
63. Macy E M, Hayes T E, Tracy R P. 1997. Variability in the measurement of Creactive protein in healthy subjects: implications for reference intervals and epidemiological applications Clin Chem 43:52-58.
64. Stamler R, Riedlinger J, Algera W F, Roberts G. 1978. Weight and blood pressure: findings in hypertension screening of 1 million Americans JAMA 240, 16071610.
65. Dyer A R, Elliott P, 1989. The INTERSALT study: relations of body mass index to blood pressure J Hum Hypertens 3, 299-308.
66. Van Gaal, L F, Wauters, M A, De Leeuw, I H. 1997. The beneficial effects of modest weight loss on cardiovascular risk factors Int JObes 21 (Suppl 1), S5-S9.

What is claimed is:

1. A synergistic composition, which is effective to increase energy expenditure in a patient, comprising an extract of brown marine vegetables comprising an effective concentration of fucoxanthin, a pharmaceutically acceptable salt of fucoxanthin, or a mixture thereof; pomegranate seed oil comprising an effective concentration of punicic acid; and a pharmaceutically acceptable carrier, wherein the extract of brown marine vegetables is present in an amount of about 25 to 75 weight percent based on the total weight of the composition and the pomegranate seed oil is present in an amount of about 25 to 75 weight percent based on the total weight of the composition.

2. The composition of claim 1, wherein the extract of brown marine vegetables further comprises a vegetable oil.

3. The composition of claim 2, wherein the vegetable oil comprises omega-3 fatty acids.

4. The composition of claim 1, wherein the composition consists of 50% by weight of the extract of brown marine vegetables; and 50% by weight of the pomegranate seed oil.

5. A synergistic composition, which is effective to increase energy expenditure in a patient, comprising an effective amount of an extract of brown marine vegetables comprising fucoxanthin, a pharmaceutically acceptable salt of fucoxanthin, or a mixture thereof; an effective amount of pomegranate seed oil comprising punicic acid; and a pharmaceutically acceptable carrier, wherein the composition is formulated in a dosage form, the dosage form providing from 1 to 50 mg/day of fucoxanthin; and b) 1 to 1000 mg/day of punicic acid.

6. An oral composition for administration to a patient comprising about 25 to 75 weight percent of an extract of brown marine vegetables comprising an effective concentration of fucoxanthin, a pharmaceutically acceptable salt of fucoxanthin, or a mixture thereof; and about 25 to 75 weight percent of pomegranate seed oil comprising an effective concentration of punicic acid, wherein the pomegranate seed oil and the extract of brown marine vegetables synergistically increase an energy expenditure rate of the patient.

7. A treatment method, comprising administering to a mammal in need thereof an effective amount of a synergistic composition which is effective to increase energy expenditure in a patient, the composition comprising an extract of brown marine vegetables comprising an effective concentration of fucoxanthin, a pharmaceutically acceptable salt of fucoxanthin, or a mixture thereof; pomegranate seed oil comprising an effective concentration of punicic acid; and a pharmaceutically acceptable carrier, wherein the extract of brown marine vegetables is present in an amount of about 25 to 75 weight percent based on the total weight of the composition and the pomegranate seed oil is present in an amount of about 25 to 75 weight percent based on the total weight of the composition; and, wherein the treatment method is a method of increasing energy expenditure rate in a patient.

8. The method of claim 7, wherein the composition further comprises a vegetable oil.

9. The method of claim 8, wherein the vegetable oil comprises omega-3 fatty acids.

10. The method of claim 7, wherein the extract of brown marine vegetables is present in an amount of about 40 to 60 weight percent based on the total weight of the composition and the pomegranate seed oil is present in an amount of about 40 to 60 weight percent based on the total weight of the composition.

11. The method of claim 7, wherein the composition is formulated in a dosage form, the dosage form providing from 1 to 1000 mg/day of fucoxanthin; and b) 1 to 1000 mg/day pomegranate seed oil.

12. The method of claim 7, wherein the composition is formulated in a dosage form, the dosage form providing from 1 to 50 mg/day of fucoxanthin; and b) 1 to 1000 mg/day pomegranate seed oil.

* * * * *